United States Patent
Czygan et al.

(10) Patent No.: US 7,130,695 B2
(45) Date of Patent: Oct. 31, 2006

(54) ARRANGEMENT FOR AND METHOD OF MONITORING, CALIBRATING AND OPTIMIZING A CONTROL OF AN ELECTROMEDICAL IMPLANT

(75) Inventors: Gerald Czygan, Buckenhof (DE); Max Schaldach, deceased, late of Erlangen (DE); by Max Schaldach, Jr., legal representative, Berlin (DE)

(73) Assignee: Biotronik Mess- und Therapiegeraete GmbH & Co. (DE)

( * ) Notice: Subject to any disclaimer, the term of this patent is extended or adjusted under 35 U.S.C. 154(b) by 613 days.

(21) Appl. No.: 10/405,976

(22) Filed: Apr. 2, 2003

(65) Prior Publication Data

US 2004/0078061 A1 Apr. 22, 2004

(30) Foreign Application Priority Data

Apr. 2, 2002 (DE) ............................... 102 15 320

(51) Int. Cl.
*A61N 1/372* (2006.01)
(52) U.S. Cl. .............................. 607/59; 607/30; 607/60
(58) Field of Classification Search .................... 607/2, 607/27, 30, 32, 59–60, 62; 600/300, 301
See application file for complete search history.

(56) References Cited

U.S. PATENT DOCUMENTS

| | | | | |
|---|---|---|---|---|
| 4,166,470 A | * | 9/1979 | Neumann | 607/33 |
| 4,644,954 A | | 2/1987 | Wittkampf | |
| 5,226,413 A | * | 7/1993 | Bennett et al. | 607/18 |
| 5,318,593 A | * | 6/1994 | Duggan | 607/9 |
| 5,342,408 A | * | 8/1994 | deCoriolis et al. | 607/32 |
| 5,540,727 A | * | 7/1996 | Tockman et al. | 607/18 |
| 5,607,460 A | | 3/1997 | Kroll et al. | |
| 5,792,204 A | * | 8/1998 | Snell | 607/32 |

FOREIGN PATENT DOCUMENTS

EP 0 148 486 A2 7/1985

OTHER PUBLICATIONS

Wetzig, T., "Technische Anwendung myokardialer Summenaktionspotentiale als Informationtraeger in der Herz-Kreislaufregelung," Universitaet Erlangen Nuemberg (Erlangen, Germany), p. 62-67, (Aug. 25, 1997).

* cited by examiner

*Primary Examiner*—Robert E. Pezzuto
*Assistant Examiner*—Jessica L. Reidel
(74) *Attorney, Agent, or Firm*—Hahn Loeser & Parks LLP; John J. Cunniff (57) ABSTRACT

An arrangement (10) for monitoring and adjusting a control of an electromedical implant (12) by means of an external control and evaluation unit (14) is made up of the electromedical implant, the external control and evaluation unit and a central, autarchically runnable evaluation logic means (30) which controls the activities of a telemetry unit (16) and a memory unit (34), which is connected to a clock and timer unit (42) and which on the basis of certain communicated data ascertains control sequences and control parameters for monitoring and adjusting the implant and co-ordinates the transmission thereof to the implant. An expert system (ES) may be adapted to assess all monitoring and adjusting tasks on a patient-individual basis.

36 Claims, 2 Drawing Sheets

ARRANGEMENT FOR AND METHOD OF MONITORING, CALIBRATING AND OPTIMIZING A CONTROL OF AN ELECTROMEDICAL IMPLANT

The invention concerns an arrangement for monitoring and adjusting a control of an electromedical implant for intracardial cardiac therapy by means of an external control and evaluation unit, an associated method and the external control and evaluation unit itself having the features set forth herein.

BACKGROUND OF THE ART

Electromedical implants such as cardiac pacemakers and defibrillators have proven to be an extraordinarily successful instrument for the electrotherapy of bradycardiac and tachycardiac rhythm disturbances. In that respect the task of implants of that kind is not restricted just to merely delivering electrical pulses to the atrium or ventricle myocardium in order there to trigger off depolarization. Rather, modern pacemakers and defibrillators involve sensors and evaluation circuits which permit controlled or regulated frequency adaptation, adaptation of pulse amplitude, pulse width and AV-time for therapy optimization purposes. In that way the aim is for the cardiovascular system of the patient to be modeled as closely as possible on the natural regulating mechanism, in terms of its reaction to physical or psychic loading (frequency- or rate-adaptive cardiac pacemaker).

Electromedical implants at the present time involve a modular design for achieving that aim. Such an implant generally includes elements such as a central control logic, a sensor arrangement for detecting body functions and for intracardial signal recording in the myocardium of the right atrium or ventricle, electrodes anchored in the myocardium, including a circuit for regulating pulse delivery, an energy source for the operating voltage, and a clock and timer unit. It will be appreciated that the specified individual components can be adapted variably to a high degree in respect of their design configuration to the respective conditions prevailing. Therefore the individual components and the appropriate combinations thereof will not be described in detail here as they are known.

Just for reasons relating to circuitry engineering it has been found appropriate for the functions of the implant to be limited to control of the pulse delivery and intracardial signal recording. More extensive tasks such as for example monitoring and optimizing the control itself can generally only be implemented to a very limited degree. That is not only due to the fact that the implementation of such complex control circuits in the limited structural space of the implant encounters at the present time the viable limits thereof. Rather, such a complex control circuit would also result in a markedly increased level of energy consumption so that the service life of the implant would be curtailed. Also, in general a defective control logic system cannot check and re-set itself. For those reasons it has been found appropriate for the electromedical implant and also an external programming device each to be provided with a transmitter and receiver. The telemetry units of the two components provides for the execution of bidirectional data exchange which includes stimulation and diagnostic parameters or recorded intracardial signal and operating parameters respectively.

U.S. Pat. No. 4,705,043 to Imran shows by way of example such an external programming device which provides for evaluation of the transmitted intracardial signals and communicates stimulation parameters to the implant. A disadvantage here is that the external electrical stimulator is an essential part of the control of the implant and, in the event of failure thereof, the implant can continue to operate at best in a predetermined basic configuration.

DE 37 22 829 C2 describes a method in which an implantable electromedical device can communicate with an external programming device, with the transmission of encoded signals. The external programming device generally comes temporarily into contact with the implant, in which case the operating mode and parameters which determine pulse triggering are communicated to an internal programming part of the implant or modified. In that arrangement the external programming device is so designed that it does not communicate with the implant independently but rather only after a given task has been predetermined for it by the programmer (generally the doctor). In practice such programming devices are correspondingly simplified in respect of their technical structure. They essentially consist of the transmitting and receiving unit and numerous interfaces, by way of which peripheral units can be connected. There is no provision for autarchical control. Accordingly the patient has to stay in the clinic in the procedure involving programming, optimization and implementation of an exercise stress test, in which respect he is additionally impeded by extensive cabling. As is known, the unusual surroundings result in what is referred to as the white coat effect in which the cardiovascular system of the patient is precisely not subject to everyday conditions and thus optimization of the stimulation effect is made difficult or entirely prevented.

SUMMARY OF THE INVENTION

Therefore the object of the present invention is to provide an arrangement for and a method of monitoring and adjusting the control of the electromedical implant for intracardial cardiac therapy with which the mobility of the patient is substantially improved. Along with that the invention seeks to improve in particular optimization of the control parameters on the basis of intracardial signals recorded under everyday conditions. The system is to operate as independently as possible and is to be capable of reacting flexibly to the possibly altered conditions without the patient having to submit to time-consuming clinical investigations.

That object is attained by the arrangement according to the invention for monitoring and adjusting a control of an electromedical implant for intracardial cardiac therapy by means of an external control and evaluation unit, and the associated method having the features described herein. The arrangement includes:

(a) the electromedical implant which includes the following components:
  a clock and timer unit for the co-ordination of a time sequence of control operations,
  an energy source for providing an operating voltage and stimulation and shock delivery,
  at least one electrode which is connected to the myocardium of the heart and which is suitable for the delivery of electrical pulses,
  a sensor which supplies measurement data about physiological parameters in the region of the heart and about internal status parameters of the implant,
  a memory unit for the storage of internal control sequences, control parameters and measurement data of the sensor,
  a telemetry unit having a transmitter and a receiver for the bidirectional data exchange with the external control and evaluation unit, and a central, autarchically runnable control logic unit which on the basis of the internal control sequences and control parameters controls the activities of the at least one electrode, the telemetry unit, the sensor and the memory unit, and (b) the external control and evaluation unit which includes the following components:

a telemetry unit having a transmitter and a receiver for the bidirectional data exchange with the electromedical implant, a timer unit for the co-ordination of a time sequence of control operations, an energy source for providing an operating voltage, a memory unit for storing control sequences, control parameters and communicated data of the implant, and a central, autarchically runnable evaluation logic unit which controls the activities of the telemetry unit and the memory unit, which is in contact with the clock and timer unit and which on the basis of the communicated data ascertains control sequences and control parameters for monitoring and adjusting the implant and co-ordinates the transmission thereof to the implant.

The autarchically runnable control logic unit of the implant firstly ensures comfortable everyday operation so that the implant and the external control and evaluation unit do not have to be permanently in telemetric contact. The control and evaluation unit with its autarchically runnable evaluation logic unit contains sequences which permit very much more extensive evaluation and optimization of the control.

In accordance with the method:

(a) in the electromedical implant a time sequence of the control operations is coordinated by a clock and timer unit, electrical pulses are delivered by way of at least one electrode connected to the myocardium of the heart, measurement data relating to physiological parameters in the region of the heart and internal status parameters of the implant are supplied by a sensor, internal control sequences, control parameters and measurement data of the sensor are stored in a memory unit, data are exchanged with the external control and evaluation unit by way of a bidirectional telemetry unit, and the activities of the at least one electrode, the telemetry unit, the sensor and the memory unit are coordinated on the basis of internal control sequences and control parameters in a central autarchically runnable control logic unit, and (b) in the external control and evaluation unit a time sequence of the control operations is coordinated in a timer unit, data are exchanged by way of a bidirectional telemetry unit with the electromedical implant, control sequences, control parameters and communicated data of the implant are stored in a memory unit, and in a central autarchically runnable evaluation logic unit the activities of the telemetry unit and the memory unit are controlled and on the basis of the communicated data control sequences and control parameters for monitoring and adjusting the implant are ascertained and the transmission thereof to the implant is coordinated.

In a preferred embodiment of the invention the arrangement includes an expert system which assesses on an individual patient basis all monitoring and adjusting tasks for intracardial cardiac therapy and divides the control sequences on which the monitoring and adjusting tasks are based into internal control sequences for the implant and external control sequences for the external evaluation and control unit. The aim of that division is to make the implant admittedly substantially autarchically operable for everyday conditions, but to cause tasks beyond that, in diagnosis and therapy, to be implemented only by way of the evaluation and control unit. Sequences which in accordance with the present patient image appear unnecessary or which are only associated with general monitoring of the operating status of the implant should if possible not be stored in the implant itself. Preferably, only the internal control sequences which include functional and diagnostic parameters which are absolutely necessary for control of the therapy functions or the diagnosis of given cardiac events remain in the implant. They also preferably include real time-dependent stimulation and diagnostic sequences. Overall therefore the control complication in the implant is to be reduced, which ultimately results in an energy saving and thus an increase in the service life.

It is further preferable if the evaluation logic unit of the external control and evaluation unit has a memory for a complex matrix into which at least the communicated data of the implant and further control parameters pass. By means of such a matrix it is possible speedily to ascertain the control parameters and control sequences on which the monitoring and adjusting tasks are based.

In a preferred embodiment of the concept of the invention the control and evaluation unit includes a first input unit for interaction with the patient. By way of that input unit the patient can input control parameters which have an influence on the operation of ascertaining the control sequences and parameters in the evaluation logic unit and thus indirectly on control of the implant. That for the first time permits the patient to play a more active part in adjusting and checking the diagnostic and stimulation parameters, which obviously can be limited by suitable programming to given regions/action of the control logic unit of the implant. It is also possible that input can be effected by way of the first input unit in various stages. Besides the possibility of directly intervening in the control, there should be a pure marker function. The patient can merely document or assess given statuses or symptoms for example by pressing a button.

It is further preferable for the external control and evaluation unit to have a second input unit for data exchange with further peripheral devices. Control sequences for the evaluation logic unit can be set up or modified and/or data can be read out of the memory unit for additional evaluation, by way of that second input unit. Conversely, time-dependent or event-dependent control parameters of the matrix can be communicated in that way. It should be emphasized at this point that the patient no longer necessarily has to be present on the spot (generally in the clinic) for such a data exchange, but it is only necessary for the external control and evaluation unit to be connected to the peripheral devices. Data exchange can then take place in particular on-line by way of a telephone connection.

In a further preferred embodiment of the invention the control parameters and control sequences ascertained by the matrix are linked with weighting factors. A time sequence of the individual monitoring and adjusting tasks is established in an interaction scheme on the basis of the weighting factors. Thus for example a time interval up to the initiation of the next routine checks can be reduced in length if the evaluation of the last measurements has furnished significant deviations from the medically necessary stimulation behavior. The external control and evaluation unit has a clock and timer unit for time co-ordination of the data exchange.

In the normal situation the weighting factors are predetermined in such a way that the impending monitoring and adjusting tasks preferably take place when the patient is in a rest phase. In that way disturbances in the course of everyday life of the patient as a consequence of extensive changes in the stimulation and diagnostic parameters are to be minimized. In the acute situation, for example if the stimulation parameters deviate substantially from the medically necessary pulse deliveries data exchange begins immediately after the interaction scheme has been prepared. It will be appreciated that the procedure for optimization of control of the implant can be effected on-line with the external control and evaluation unit, that is to say data exchange can take place one after the other until optimum conditions obtain. Preferably also a series of the control parameters and control sequences communicated to the implant during the interaction of the external control and evaluation unit is established by the weighting factors. In that way for example optimization of the stimulation parameters, which is more significant for the patient, can be preferred to routine checking of the implant.

An external evaluation and control unit which is modified in the above-indicated manner is claimed separately.

BRIEF DESCRIPTION OF THE DRAWINGS

Further preferred configurations of the invention are set forth by the other features recited in the appendant claims. The invention is described in greater detail hereinafter in an embodiment by way of example with reference to drawings in which:

DETAILED DESCRIPTION OF THE INVENTION

Figure 1:
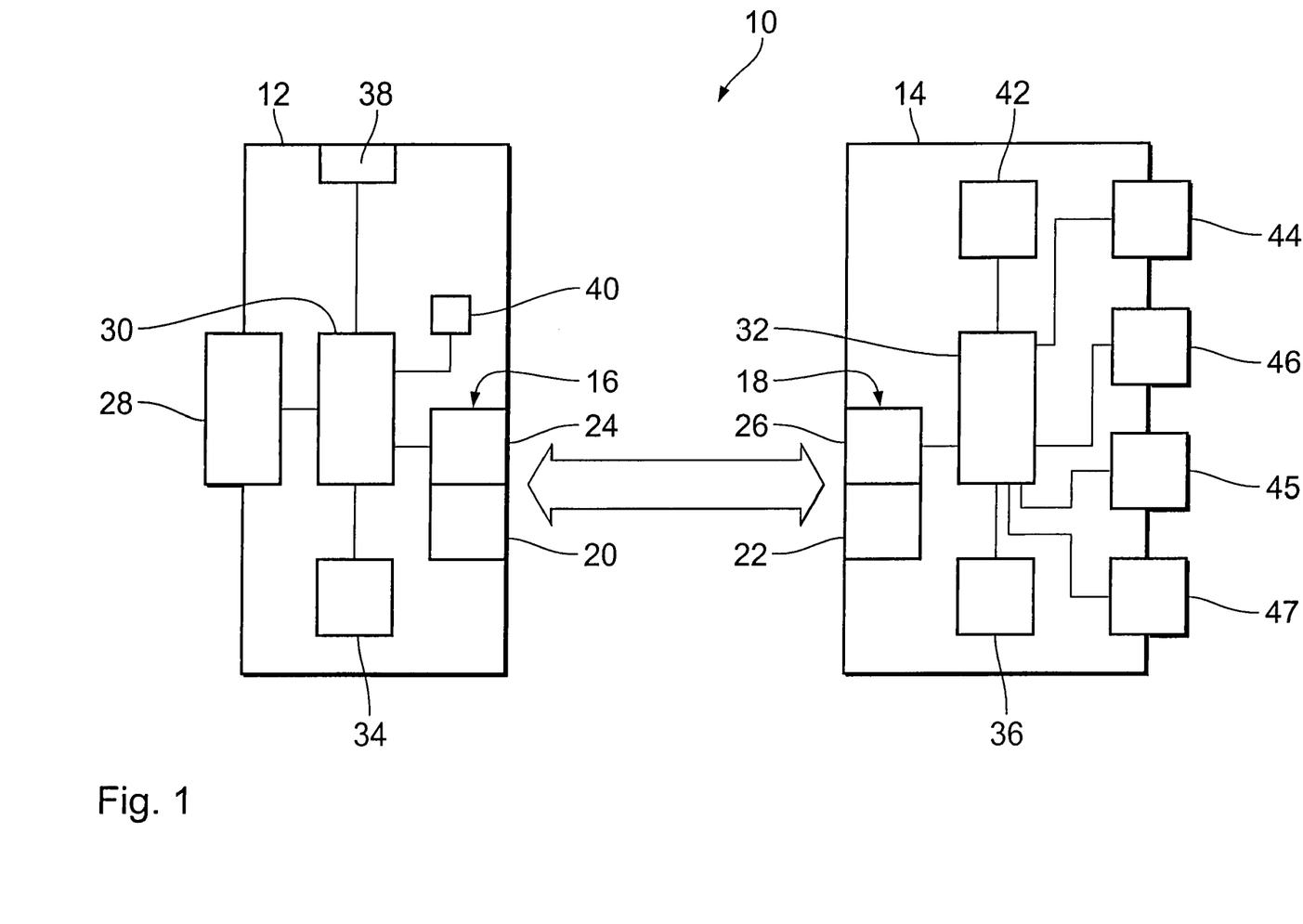
FIG. 1 is diagrammatic view showing the principle involved in relation to the mode of operation of an arrangement for monitoring and adjusting a control of an electromedical implant for intracardial cardiac therapy by an external control and evaluation unit.

FIG. 1 shows the structure in principle of an arrangement 10 for monitoring and adjusting a control of an electromedical implant 12 for intracardial cardiac therapy by an external control and evaluation unit 14. The electromedical implant 12 is for example a rate-adaptive cardiac pacemaker.

The implant 12 and the control and evaluation unit 14 each include a telemetry unit 16, 18 with a respective transmitter 20, 22 and receiver 24, 26, which are suitable for the bidirectional telemetric transmission of data. The data transmitted telemetrically contain for example items of patient information such as the implantation date, the date of the last aftercare, details relating to the symptoms and so forth. In addition diagnostic information, for example relating to atrial or ventricular diagnosis and stimulation can be communicated. In addition battery and electrode parameters, in particular the currently prevailing values of battery voltage, internal battery resistance and current consumption are transmitted in order to permit a realistic estimate of the operating time to be expected. Furthermore measurement data which is discussed in greater detail hereinafter from a sensor 28 and control sequences and parameters for a control logic unit 30 of the implant 12 and evaluation logic unit 32 of the evaluation and control unit 14 can be exchanged by way of the telemetry units 16, 18. The structure and mode of operation of such telemetry units 16, 18 have long been known from the state of the art and are therefore not to be discussed in greater detail at this point.

The implant 12 further includes a sensor 28 with which parameters of physical or physiological nature which can be used for controlling or regulating the therapy can be directly detected. Examples in that respect are piezoelectric oscillators or capacitive sensors for detecting body activity and kinetic energy, sensors for detecting a central-venous blood temperature or oxygen saturation, pH-value sensors, sensors for detecting a respiration rate, a respiration minute volume and the beat volume of the heart, sensors for determining contractibility or contraction dynamics and sensors for detecting evoked myocardium potentials. In this case also the sensor 28 will not be described in greater detail as they have already long been known from the state of the art.

Both the implant 12 and also the control and evaluation unit 14 include a memory unit 34, 36. The memory unit 34 of the implant 12 serves for the storage of internal control sequences, control parameters and measurement data of the sensor 28 and the memory unit 36 of the control and evaluation unit 14 serves for the storage of control sequences, control parameters and transmitted data.

The implant 12 has an electrode 38 for stimulation and diagnostic purposes. The electrode 38 is connected to the myocardium of the heart and is suitable for the delivery of electrical pulses. In principle it is possible to use any electrode known from the state of the art if it can be employed for the stimulation and diagnostic tasks to be performed. In addition the implant 12 has an energy source (not shown here) for providing the operating voltage (generally a battery).

The implant 12 includes a suitable circuit with which it is possible to implement the control logic unit 30 which co-ordinates the activities of all the system components present in regard to stimulation and diagnosis on the basis of internal control sequences and control parameters. The control logic unit is autarchically runnable, that is to say on its own it can ensure all the stimulation and diagnostic tasks relating to everyday life. A central control logic unit 30 of that kind is usually an integrated semiconductor circuit connected to other system components, in particular the means for telemetry as indicated at 16, 18, sensor 28, memory unit 34, 36 and the electrode actuation unit. Attention is again directed here to the numerous design configurations described in the state of the art. The functional components of the control logic unit 30, which serve to carry the invention into effect, are in practice implemented in the form of software and are inseparably interwoven with the rest of the pacemaker structure.

For a cardiac pacemaker which has at least one electrode 38 for pulse excitation and diagnosis in the right atrium and ventricle, the individual tasks of the pacemaker control logic unit 30 can be implemented in the form of a binary automatic device which can assume different states in dependence on given time intervals and detected signals. The most important time intervals for the control procedure relate for example to periods of time which can pass at a maximum between two natural pulses of the respective chambers without a stimulus being triggered. An AV-delay is shortened in modern pacemakers on the one hand after detected events in relation to stimulated events in order to take account of the delay between atrium stimulus and actual atrium depolarization (latency time compensation). On the other hand the AV-delay is shortened in dependence on frequency to simulate a natural dromotrophy in order to ensure optimum synchronization even at higher heart rates (dynamic AV-time). In regard to details relating to such a control logic unit 30 attention is directed to the book by Schaldach, Electrotherapy of the Heart, Springer Verlag, Berlin, 1992. It will be self-evident that a clock and timer unit 40 must be provided for the implementation of a control logic unit 30 of that kind. The clock and timer unit 40 is for example an oscillator quartz. A clock and timer unit 42 is also required on the part of the external control and evaluation unit 14 for tine co-ordination of the control procedures.

The external control and evaluation unit 14 further includes two input units 44, 46. The first input unit 44 is intended to permit interaction on the part of the patient. That is intended to provide that the patient can appropriately react to physical hardships which possibly occur and can influence control of the implant 12. In that respect, an extent of the intervention options can be defined by the evaluation logic unit 32, in dependence on the individual skills of the patient. It is also possible for the input to be effected in various stages by way of the first input unit 44. A pure marker function should be possible, besides the direct option of intervention in the control arrangement. The patient can merely document or assess given symptoms or states for example by pressing a button.

The second input unit 46 is intended to permit data exchange with further peripheral devices. If for example extensive statistical evaluations involving a high level of computing expenditure are to be carried out or if data put into intermediate storage in the control and evaluation unit 14 are to be fed to an output device, a communication with those peripheral devices can be effected by way of the second input unit 46. In the reverse direction, the control sequences and control parameters of the evaluation logic unit 32 itself can be adapted to new requirements and can possibly be completely set up afresh. The second input unit 46 can in particular include a modem for connection to a telephone line so that remote maintenance of the evaluation and control device 14 is possible.

A further input unit 45 is provided for the connection of external sensors to the control and evaluation unit 14. Sensors of that kind can be in particular position sensors, acceleration sensors, sensors for recording a surface ECG or blood pressure sensors. The measurement data recorded by the sensors pass into the evaluation logic unit 32, in the form of control values. It is also possible for one or more sensors to be already fixedly integrated into the control and evaluation unit 14 (input unit 47). However mobility and ease of handling of the specific control and evaluation unit 14 are to the fore in terms of implementation.

Figure 2:
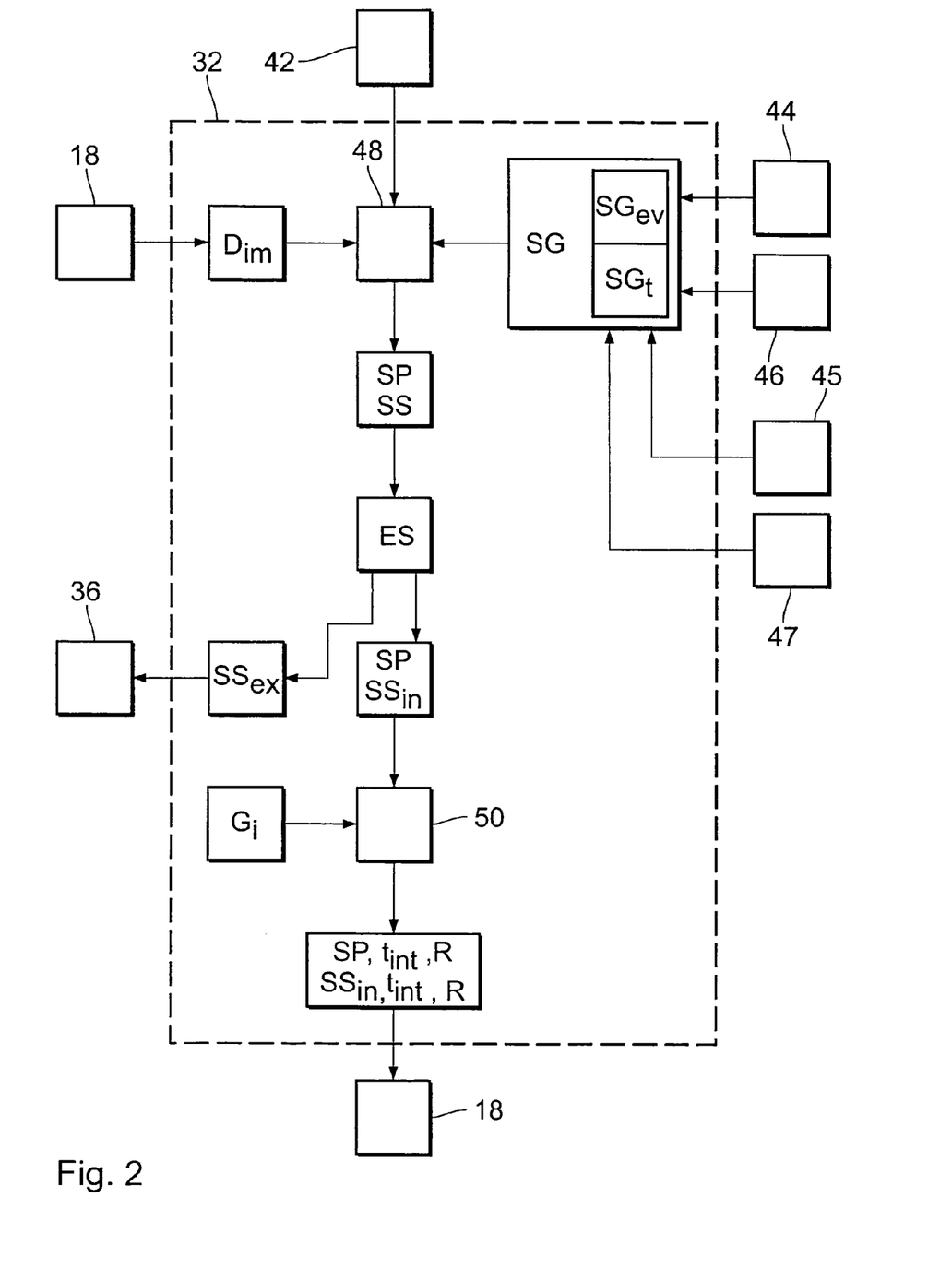
FIG. 2 shows a functional block circuit diagram of an evaluation logic unit of the external control and evaluation unit.

As shown in FIG. 2, the external control and evaluation unit 14 further includes the autarchically runnable evaluation logic unit 32 which monitors and adjusts control of the implant 12 in dependence on the telemetrically communicated data of the implant 12 and control values which are discussed in greater detail hereinafter. For that purpose the control and evaluation unit 14 has a memory 48 organized in matrix-like manner. The memory 48 can be produced using common semiconductor technology or can be implemented at least in parts in software form. Such an evaluation logic unit 32 also includes functional components such as a processor unit for data processing, working memories and further electronic elements which for example permit communication with the input units 44, 45, 46, 47, the telemetry unit 16 and the sensor 28. In practice the functional components which serve to carry the invention into effect are in part embodied in software form and inseparably interwoven with the rest of the control and evaluation structure. Electronic systems of that kind have long been known and vary considerably in their design as a consequence of technological progress so that a more detailed description will not be set forth here. An energy source (not shown) is required to supply the necessary operating voltage. A rechargeable accumulator for example serves for that purpose.

FIG. 2 diagrammatically shows the mode of operation of an autarchically runnable evaluation logic unit 32 of the control and evaluation unit 14. For that purpose the evaluation logic unit 32 has the complex central matrix in the memory 48, into which pass the transmitted data $D_{im}$ of the implant 12 and the control values SG. A time signal t is also brought into play by way of the clock and timer unit for co-ordination in respect of time. The control values SG can be systematically subdivided into time-dependent control values $SG_t$ and event-dependent control values $SG_{ev}$.

The time-dependent control values $SG_t$ include inter alia parameters for monitoring tasks which compel at predeterminable time intervals:

routine checking of the entire control logic unit 30 of the implant 12 or sub-regions of the control logic unit, routine checking of the entire control logic unit 30 of the implant 12 or sub-regions of the control logic unit as a consequence of an input effected by the patient, and routine checking of the entire control logic unit 30 of the implant 12 or sub-regions of the control logic unit as a result of a presetting by means of suitable peripheral devices.

Control routines of that kind on the part of the evaluation logic unit 32 are intended to ensure trouble-free operation of the implant 12 over long periods of time.

Under certain circumstances it is appropriate to provide that event-dependent control values $SG_{ev}$ pass into the matrix of the evaluation logic unit 32. In that respect event-dependent control values $SG_{ev}$ which fall to be considered are in particular parameters for monitoring and adjusting tasks, which:

are inputted by the patient by way of the first input unit 44, are predetermined by means of suitable peripheral devices by way of the second input unit 46, or which are ascertained by means of suitable sensors by way of the input units 45, 47.

The time- and event-dependent control values $SG_t$, $SG_{ev}$ pass in combined form as control values SG into the matrix. They are used together with the data $D_{im}$ of the implant 12 for ascertaining the control sequences SS and control parameters SP for monitoring and adjusting tasks to be performed.

In this sense the term control sequence SS is used to denote a programmed chain of commands, the execution of which leads to the presetting of given control parameters SP for adjusting members present in the implant control system. The control parameters SP are accordingly ascertained on the spot. If the control parameters SP were already ascertained in the evaluation and control unit 14 and transmitted telemetrically to the implant 12, transmission can be effected directly to the adjusting members of the implant 12. In that way it is possible to forego storing the control sequence SS in the implant 12.

The evaluation logic unit 32 includes an expert system ES which on a patient-individual basis assesses all monitoring and adjusting tasks for intracardial cardiac therapy. The expert system ES serves to divide the control sequences SS on which the monitoring and adjusting tasks are based into internal control sequences $SS_{in}$ for the implant 12 and external control sequences $SS_{ex}$ for the external evaluation and control unit 14. That is intended on the one hand to shorten a duration of data transmission, by a reduction in the amount of data to be exchanged. In addition, only the control sequences SS which are actually necessary for autarchic runnability are to be stored in the implant 12. That saves on memory space and reduces the level of energy consumption for those sequences are now consequently only executed in the evaluation and control unit 14. The control parameters resulting therefrom are then transmitted telemetrically.

The internal control sequences $SS_{in}$ include the stimulation and diagnosis sequences which are absolutely necessary for control of the stimulation function or diagnosis of given cardiac events. If for example the patient suffers from normotopic tachycardia of the right atrium without other stimulation disturbances, there is no need to predetermine ventricular control sequences. It is only if more detailed evaluation in the evaluation and control unit 14 indicates that there is also a meaningful need for ventricular cardiac therapy that the necessary control sequences SS are transmitted. Control sequences SS which are to be installed at any event on the implant 12 obviously concern real time-dependent stimulation and diagnostic sequences.

The internal control sequences $SS_{in}$ and control parameters SP remaining after selection by the expert system ES are additionally interlinked with weighting factors $G_i$. On the one hand a time interval $t_{int}$ in which the monitoring and adjusting tasks are to take place is to be established on the basis of the weighting factors $G_i$. On the other hand it is also possible to determine a series R of the internal control sequences $SS_{in}$ and control parameters SP which are transmitted during the interaction of the external control and evaluation unit 14 to the implant 12, for the impending monitoring and adjusting tasks (producing an interaction scheme 50). Thus it is appropriate to implement re-setting of the control logic unit 30 prior to monitoring thereof. In the normal situation the weighting factors $G_i$ are so selected that the time interval $t_{int}$ for monitoring and adjustment occurs when the patient is in a rest phase. In the case of acute events, for example a diagnosed active ectopic stimulation disturbance or as a consequence of a patient input, the time interval $t_{int}$ is so predetermined that it begins immediately after the production of the interaction scheme 50. Under some circumstances the connection between the external control and evaluation unit 14 and the implant 12 is maintained until optimization of the control is concluded. Data exchange can then take place for example one after the other.

The interaction scheme 50 includes the individual tasks which are to be executed as a consequence of matrix evaluation for monitoring and adjustment of the control logic unit 30 of the implant 12. The series R and the time interval $t_{int}$ are established for the tasks to be performed and, as soon as there is telemetric contact they are executed. To ensure the complex monitoring and adjusting tasks, it can be provided that the external control and evaluation unit 14 has an acoustic output unit. If the period of time between the last telemetric contact has already no longer materialized for a predetermined length of time or if urgent tasks are to be executed in the interaction scheme 50 the patient can have attention drawn to the fact of the need to produce the contact, by means of acoustic signals.

The above-described procedure can be used both for monitoring and adjusting the stimulation parameters and also for monitoring and adjusting the diagnostic parameters. Thus for example differentiated analysis of cardiac activity may be necessary after evaluation of the data $D_{im}$ transmitted by the implant 12 in order with the information obtained in that way still further to improve the stimulation or to check the medical necessity therefor respectively.

| List of references | |
|---|---|
| 10 | arrangement |
| 12 | electromedical implant |
| 14 | external control and evaluation unit |
| 16, 18 | telemetry unit |
| 20, 22 | transmitter |
| 24, 26 | receiver |
| 28 | sensor means |
| 30 | control logic means |
| 32 | evaluation logic means |
| 34, 36 | memory unit |
| 38 | electrode |
| 40, 42 | clock and timer |
| 44, 45, 46, 47 | input units |
| 48 | matrix-type memory |
| 50 | interaction scheme |
| $D_{im}$ | transmitted data from the implant 12 |
| $G_i$ | weighting factor |
| R | series of the monitoring and adjusting tasks |
| SG | control value |
| $SG_t$ | time-dependent control value |
| $SG_{ev}$ | event-dependent control value |
| SP | control parameter |
| SS | control sequence |
| $SS_{in}$ | internal control sequence |
| $t_{int}$ | time interval for the monitoring and adjusting task |

The invention claimed is:

1. An arrangement for monitoring and adjusting control of an electromedical implant for intracardial cardiac therapy of a patient by an external control and evaluation unit, wherein the arrangement comprises:
   (a) the electromedical implant, which comprises:
       a clock and timer unit for the co-ordination of a time sequence of control operations,
       an energy source for providing an operating voltage and for stimulation and shock delivery,
       at least one electrode which is adapted for connection to myocardium of a heart and which is adapted for the delivery of electrical pulses,
       a sensor which supplies measurement data about physiological parameters in a region of the heart and about internal status parameters of the implant,
       a memory unit for a storage of internal control sequences, control parameters and measurement data of the sensor,
       a telemetry unit having a transmitter and a receiver for bidirectional data exchange with the external control and evaluation unit, and
       a central, autarchically runnable control logic unit which controls activities of the at least one electrode, the telemetry unit, the sensor and the memory unit on the basis of the internal control sequences and control parameters, and
   (b) the external control and evaluation unit, which comprises:
       a telemetry unit having a transmitter and a receiver for bidirectional data exchange with the electromedical implant,
       a clock and timer unit for the co-ordination of a time sequence of control operations,
       an energy source for providing an operating voltage,
       a memory unit for storing control sequences, control parameters and communicated data of the implant,
       a central, autarchically runnable evaluation logic unit which controls the activities of the telemetry unit and the memory unit, which is connected to the clock and timer unit and which on the basis of the communicated data ascertains control sequences and control parameters for monitoring and adjusting the implant and co-ordinates the transmission thereof to the implant, and wherein the evaluation logic unit further comprises an expert system which is adapted to assess all monitoring and adjusting tasks for the intracardial cardiac therapy on a patient-individual basis and divides the control sequences on which the monitoring and adjusting tasks are based into internal control sequences for the implant and external control sequences for the external evaluation and control unit, and wherein the evaluation logic unit of the external control and evaluation unit has a memory for a complex matrix into which at least the transmitted data of the implant and the control values pass and which delivers the control parameters and control sequences on which the monitoring and adjusting tasks are based.

2. The arrangement of claim 1, wherein: the internal control sequences include therapy and diagnostic sequences which are absolutely necessary for controlling therapy functions or diagnosis of given cardiac events respectively.

3. The arrangement of claim 2, wherein the external control and evaluation unit further comprises:
a first input unit for interaction with the patient, by way of which the patient can input controls values and influence the evaluation logic unit or can implement markings and assessments of given states or symptoms.

4. The arrangement of claim 3, wherein the external control and evaluation unit further comprises:
a second input unit for data exchange with further peripheral devices, by way of which the patient can input control values, and control sequences for the evaluation logic unit can be modified or produced afresh and/or data can be read out of the memory unit for additional evaluation.

5. The arrangement of claim 4, wherein the external control and evaluation unit further comprises:
a further input unit for data exchange with external sensors, by way of which control values can be inputted.

6. The arrangement of claim 5, wherein the external control and evaluation unit further comprises:
a further input unit with integrated sensors, by way of which control values can be inputted.

7. The arrangement of claim 6, wherein:
the evaluation logic unit of the external control and evaluation unit has a memory adapted to maintain a complex matrix into which at least the transmitted data of the implant and the control values pass and which delivers the control parameters and control sequences on which the monitoring and adjusting tasks are based.

8. The arrangement of claim 7, wherein:
the evaluation logic unit is such that the control parameters and/or control sequences which are provided for the telemetric data exchange are interlinked with weighting factors, on the basis of which a time progression and/or a series of transmission of the individual monitoring and adjusting tasks is established in an interaction scheme.

9. The arrangement of claim 3, wherein the external control and evaluation unit further comprises:
a further input unit for data exchange with external sensors, by way of which control values can be inputted.

10. The arrangement of claim 3, wherein the external control and evaluation unit further comprises:
a further input unit with integrated sensors, by way of which control values can be inputted.

11. The arrangement of claim 1, wherein: the internal control sequences include real time-dependent therapy and diagnostic sequences.

12. The arrangement of claim 11, wherein: the external control and evaluation unit further comprises a first input unit for interaction with the patient, by way of which the patient can input controls values and influence the evaluation logic unit or can implement markings and assessments of given states or symptoms.

13. The arrangement of claim 12, wherein the external control and evaluation unit further comprises: a second input unit for data exchange with further peripheral devices, wherein the second input unit is adapted to allow the patient to input control values, to modify control sequences for the evaluation logic unit or to produce control sequences for the evaluation logic unit afresh, to allow data to be read out of the memory unit for additional evaluation, or a combination thereof.

14. The arrangement of claim 13, wherein the external control and evaluation unit further comprises: a further input unit for data exchange with external sensors, by way of which control values can be inputted.

15. The arrangement of claim 14, wherein the external control and evaluation unit further comprises: a further input unit with integrated sensors, by way of which control values can be inputted.

16. The arrangement of claim 15, wherein: the evaluation logic unit is such that the control parameters and/or control sequences which are provided for the telemetric data exchange are interlinked with weighting factors, on the basis of which a time progression and/or a series of transmission of the individual monitoring and adjusting tasks is established in an interaction scheme.

17. An external evaluation and control unit for an arrangement as set forth in claim 16 and adapted for carrying out a method comprising
using the clock and timer unit to co-ordinate a time sequence of the control operations,
delivering electrical pulses by way of the at least one electrode adapted to be connected to myocardium of the heart,
supplying measurement data relating to physiological parameters in the region of the heart and internal status parameters of the implant from the sensor to the memory unit,
storing internal control sequences, control parameters and measurement data of the sensor in the memory unit, and
co-ordinating the activities of the at least one electrode, the telemetry unit, the sensor and the memory unit on the basis of the internal control sequences and control parameters in a central autarchically runnable control logic unit, and
exchanging data between the electromedical implant and the external control and evaluation unit by way of a bidirectional telemetry unit,
coordinating a time sequence of the control operations by the timer unit,
storing control sequences, control parameters and communicated data of the implant in the memory unit, and
controlling the activities of the telemetry unit and the memory unit in a central autarchically runnable evaluation logic unit and ascertaining the communicated data control sequences and control parameters for monitoring and adjusting the implant and co-ordinating the transmission thereof to the implant;

wherein the evaluation logic unit of the external control and evaluation unit includes a memory adapted to maintain a complex matrix into which at least the transmitted data of the implant and the control values pass and which delivers the control parameters and control sequences on which the monitoring and adjusting tasks are based;

wherein the control values include time-dependent control values that include a factor which compels routine checking of the entire control of the implant or sub-regions of said control at predeterminable time intervals;

wherein the control values further include event-dependent control values that include a factor which can be predetermined by way of further input units at the external control and evaluation unit with integrated or external sensors, and wherein the factor passes into the evaluation and compels monitoring or adjustment of the entire control of the implant or sub-regions of the control at predeterminable time intervals;

wherein the control parameters and control sequences are interlinked with weighting factors, on the basis of which a time progression of the individual monitoring and adjusting tasks is established in an interaction scheme;

wherein the weighting factors serve to establish a series of the monitoring and adjusting tasks which are transmitted during the interaction of the external control and evaluation unit to the implant.

18. The arrangement of claim 15, wherein:
the evaluation logic means of the external control and evaluation unit has a memory adapted to maintain a complex matrix into which at least the transmitted data of the implant and the control values pass and which delivers the control parameters and control sequences on which the monitoring and adjusting tasks are based.

19. The arrangement of claim 18, wherein:
the evaluation logic unit is such that the control parameters and/or control sequences which are provided for the telemetric data exchange are interlinked with weighting factors, on the basis of which a time progression and/or a series of transmission of the individual monitoring and adjusting tasks is established in an interaction scheme.

20. The arrangement of claim 1, wherein the external control and evaluation unit further comprises:
a first input unit for interaction with the patient, by way of which the patient can input controls values and influence the evaluation logic unit or can implement markings and assessments of given states or symptoms.

21. The arrangement of claim 20, wherein the external control and evaluation unit further comprises:
a second input unit for data exchange with further peripheral devices, by way of which the patient can input control values, and control sequences for the evaluation logic unit can be modified or produced afresh and/or data can be read out of the memory unit for additional evaluation.

22. The arrangement of claim 20, wherein the external control and evaluation unit further comprises:
a further input unit for data exchange with external sensors, by way of which control values can be inputted.

23. The arrangement of claim 20, wherein the external control and evaluation unit further comprises:
a further input unit with integrated sensors, by way of which control values can be inputted.

24. A method of monitoring an electromedical implant and adjusting control of the electromedical implant for intracardial cardiac therapy of a patient by means of an external control and evaluation unit, wherein the method comprises:
providing an electromedical implant containing a clock, a timer unit, at least one electrode connected adapted to be connected to myocardium of a heart, a sensor, a memory unit and a central autarchically runnable control logic unit and providing an external control and evaluation unit containing a bidirectional telemetry unit, a timer unit, and a memory unit, and
using the clock and timer unit to co-ordinate a time sequence of control operations,
delivering electrical pulses by way of the at least one electrode,
supplying measurement data relating to physiological parameters in a region of the heart and internal status parameters of the implant from the sensor to the memory unit,
storing internal control sequences, control parameters and measurement data of the sensor in the memory unit, and
co-ordinating the activities of the at least one electrode, the telemetry unit, the sensor means and the memory unit on the basis of the internal control sequences and control parameters in a central autarchically runnable control logic unit, and
exchanging data between the electromedical implant and the external control and evaluation unit by way of a bidirectional telemetry unit,
co-ordinating a time sequence of the control operations by the timer unit,
storing control sequences, control parameters and communicated data of the implant in the memory unit, and
controlling the activities of the telemetry unit and the memory unit in a central autarchically runnable evaluation logic unit and ascertaining the communicated data control sequences and control parameters for monitoring and adjusting the implant and co-ordinating the transmission thereof to the implant;
wherein the evaluation logic unit of the external control and evaluation unit includes a memory adapted to maintain a complex matrix into which at least the transmitted data of the implant and the control values pass and which delivers the control parameters and control sequences on which the monitoring and adjusting tasks are based.

25. The method of claim 24, wherein the control values include time-dependent control values.

26. The method of claim 25, wherein the time-dependent control values include a factor which compels routine checking of the entire control of the implant or sub-regions of said control at predeterminable time intervals.

27. The method of claim 26, wherein the control values include event-dependent control values.

28. The method of claim 27, wherein the event-dependent control values include a factor which can be inputted by the patient by way of the first input unit at the external control and evaluation unit, and wherein the factor passes into the evaluation, and compels monitoring or adjustment of the entire control of the implant or sub-regions of the control at predeterminable time intervals.

29. The method of claim 27, wherein the event-dependent control values include a factor which can be predetermined by way of the second input unit at the external control and evaluation unit by suitable peripheral devices, and wherein the factor passes into the evaluation and compels monitoring or adjustment of the entire control of the implant or sub-regions of the control at predeterminable time intervals.

30. The method of claim 27, wherein the event-dependent control values include a factor which can be predetermined by way of further input units at the external control and evaluation unit with integrated or external sensors, and wherein the factor passes into the evaluation and compels monitoring or adjustment of the entire control of the implant or sub-regions of the control at predeterminable time intervals.

31. The method of claim 30, wherein the control parameters and control sequences are interlinked with weighting factors, on the basis of which a time progression of the individual monitoring and adjusting tasks is established in an interaction scheme.

32. The method of claim 31, wherein the weighting factors serve to establish a series of the monitoring and adjusting tasks which are transmitted during the interaction of the external control and evaluation unit to the implant.

33. The method of claim 32, wherein in the normal situation the weighting factors are so predetermined that the impending monitoring and adjusting tasks are carried out in a rest phase of the patient.

34. The method of claim 32, wherein in the acute situation the weighting factors are so predetermined that the impending monitoring and adjusting tasks begin immediately after production of the interaction scheme.

35. The method of claim 25, wherein the time-dependent control values include a factor which can be inputted by the patient by way of a first input unit at the external control and evaluation unit and compels routine checking of the entire control of the implant or sub-regions of the control at predeterminable time intervals.

36. The method of claim 25, wherein the time-dependent control values include a factor which can be predetermined by way of a second input unit at the external control and evaluation unit by suitable peripheral devices and which compels routine checking of the entire control of the implant or sub-regions of the control.

* * * * *